(12) United States Patent
Maurus

(10) Patent No.: US 9,867,621 B2
(45) Date of Patent: Jan. 16, 2018

(54) LIGATOR SYSTEM WITH AN INTERMEDIATE RING BETWEEN THE RING BANDS

(71) Applicant: Michael Maurus, Immenstadt (DE)

(72) Inventor: Michael Maurus, Immenstadt (DE)

( * ) Notice: Subject to any disclaimer, the term of this patent is extended or adjusted under 35 U.S.C. 154(b) by 349 days.

(21) Appl. No.: 14/759,575

(22) PCT Filed: Dec. 12, 2013

(86) PCT No.: PCT/EP2013/076390
§ 371 (c)(1),
(2) Date: Jul. 7, 2015

(87) PCT Pub. No.: WO2014/108270
PCT Pub. Date: Jul. 17, 2014

(65) Prior Publication Data
US 2015/0366564 A1     Dec. 24, 2015

(30) Foreign Application Priority Data

Jan. 8, 2013   (DE) .................... 20 2013 100 076 U

(51) Int. Cl.
*A61B 17/10* (2006.01)
*A61B 17/12* (2006.01)
*A61B 17/00* (2006.01)

(52) U.S. Cl.
CPC .............. *A61B 17/12013* (2013.01); *A61B 2017/00818* (2013.01); *A61B 2017/12018* (2013.01)

(58) Field of Classification Search
CPC .... A61B 17/12013; A61B 2017/12018; A61B 2017/00818
See application file for complete search history.

(56) References Cited

U.S. PATENT DOCUMENTS

| 3,958,576 A | * | 5/1976 | Komiya | A61B 17/083 24/456 |
| 4,226,239 A | * | 10/1980 | Polk | A61B 17/12013 128/831 |
| 5,269,789 A | * | 12/1993 | Chin | A61B 17/12013 606/140 |
| 5,356,416 A | * | 10/1994 | Chu | A61B 17/12013 606/140 |
| 5,398,844 A | * | 3/1995 | Zaslavsky | A61B 17/12013 221/208 |

(Continued)

FOREIGN PATENT DOCUMENTS

DE   19834263 A1   2/2000
DE   69331394 T2   8/2002

*Primary Examiner* — Eric Rosen
*Assistant Examiner* — Son Dang

(57) ABSTRACT

A ligator system for applying an expanded ligator ring to an anatomical region of a living being to be ligatured by the ring in its relaxed state, which comprises a ligator with a holding tube, which receives inside it the anatomical region to be ligatured in each case and with its outer surface keeps a number of ligator rings arranged one behind the other expanded, wherein the ligator system comprises at least one intermediate ring, which is arranged on the holding tube between two ligator rings and keeps the two ligator rings at a distance from one another in the direction of the longitudinal axis of the holding tube.

11 Claims, 2 Drawing Sheets

(56) References Cited

U.S. PATENT DOCUMENTS

| | | | | |
|---|---|---|---|---|
| 5,462,559 A | * | 10/1995 | Ahmed | A61B 17/12013 606/139 |
| 5,507,797 A | * | 4/1996 | Suzuki | A61B 17/12013 606/139 |
| 5,624,453 A | * | 4/1997 | Ahmed | A61B 17/12013 606/139 |
| 5,681,328 A | * | 10/1997 | Lamport | A61B 17/12013 606/140 |
| 5,741,273 A | * | 4/1998 | O'Regan | A61B 17/12013 606/1 |
| 5,913,865 A | * | 6/1999 | Fortier | A61B 17/12013 606/140 |
| 5,972,009 A | * | 10/1999 | Fortier | A61B 17/12013 606/151 |
| 5,980,537 A | * | 11/1999 | Ouchi | A61B 17/12013 606/140 |
| 6,042,591 A | * | 3/2000 | Mears | A61B 17/12013 606/140 |
| 6,059,719 A | | 5/2000 | Yamamoto et al. | |
| 6,059,797 A | * | 5/2000 | Mears | A61B 17/12009 606/139 |
| 6,136,009 A | * | 10/2000 | Mears | A61B 17/12009 606/140 |
| 6,235,040 B1 | * | 5/2001 | Chu | A61B 17/12013 606/139 |
| 6,280,452 B1 | * | 8/2001 | Mears | A61B 17/12013 606/139 |
| 6,436,108 B1 | * | 8/2002 | Mears | A61B 17/12013 606/139 |
| 6,685,713 B1 | * | 2/2004 | Ahmed | A61B 17/12013 606/139 |
| 6,730,101 B1 | * | 5/2004 | Peifer | A61B 17/12013 606/139 |
| 6,974,466 B2 | * | 12/2005 | Ahmed | A61B 17/12013 606/139 |
| 7,727,249 B2 | * | 6/2010 | Rahmani | A61B 17/12013 606/140 |
| 8,262,677 B2 | * | 9/2012 | Goto | A61B 1/00087 606/140 |
| 8,506,477 B2 | * | 8/2013 | Waller | A61B 17/12013 600/104 |
| 8,591,525 B2 | * | 11/2013 | Ikeda | A61B 17/12013 128/831 |
| 8,728,096 B2 | * | 5/2014 | Doughty | A61B 17/12013 606/140 |
| 8,821,515 B2 | * | 9/2014 | Richardson | A61B 17/12013 606/140 |
| 8,974,474 B2 | * | 3/2015 | Kamler | A61B 17/12013 606/140 |
| 9,370,370 B2 | * | 6/2016 | Abi-Kheirs | A61B 17/1227 |
| 9,629,649 B2 | * | 4/2017 | Smith | A61B 17/320016 |
| 2004/0176784 A1 | * | 9/2004 | Okada | A61B 17/1285 606/142 |
| 2006/0256041 A1 | | 11/2006 | Hoffman et al. | |
| 2008/0004622 A1 | * | 1/2008 | Coe | A61B 17/12013 606/50 |
| 2008/0140089 A1 | * | 6/2008 | Kogiso | A61B 17/122 606/142 |
| 2008/0255412 A1 | * | 10/2008 | Surti | A61B 17/12013 600/104 |
| 2008/0287965 A1 | * | 11/2008 | Ducharme | A61B 17/12013 606/140 |
| 2011/0077666 A1 | * | 3/2011 | McCahon | A61B 17/12013 606/139 |
| 2011/0106116 A1 | | 5/2011 | Ducharme et al. | |
| 2012/0078272 A1 | * | 3/2012 | Smith | A61B 17/12009 606/140 |
| 2012/0239061 A1 | * | 9/2012 | Mathur | A61F 5/0083 606/140 |

\* cited by examiner

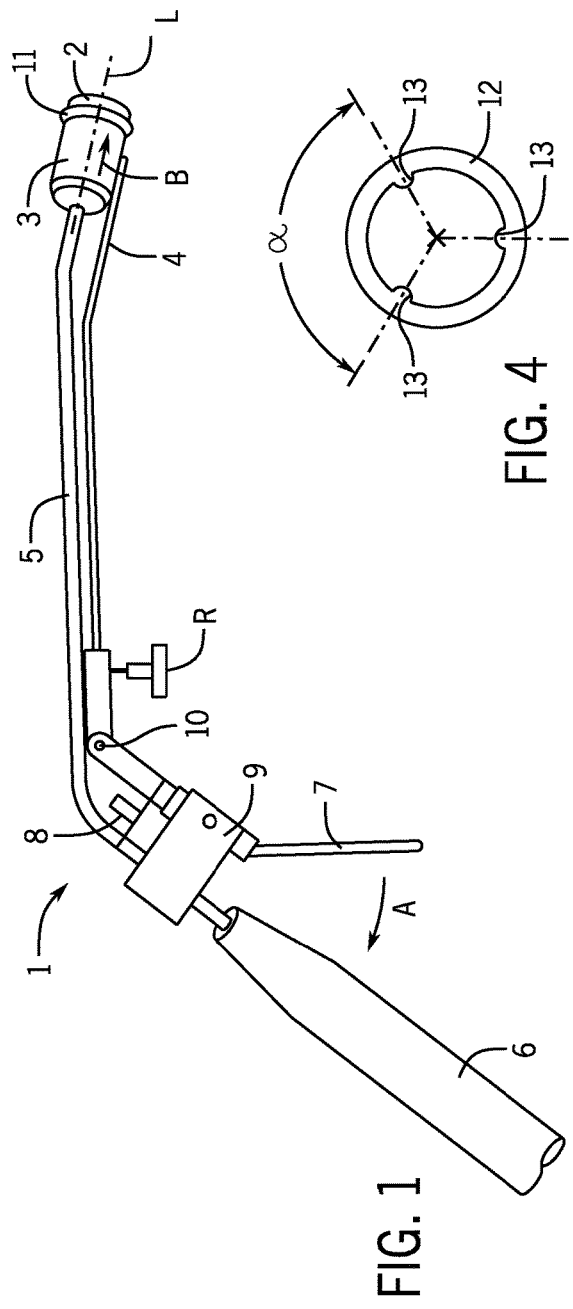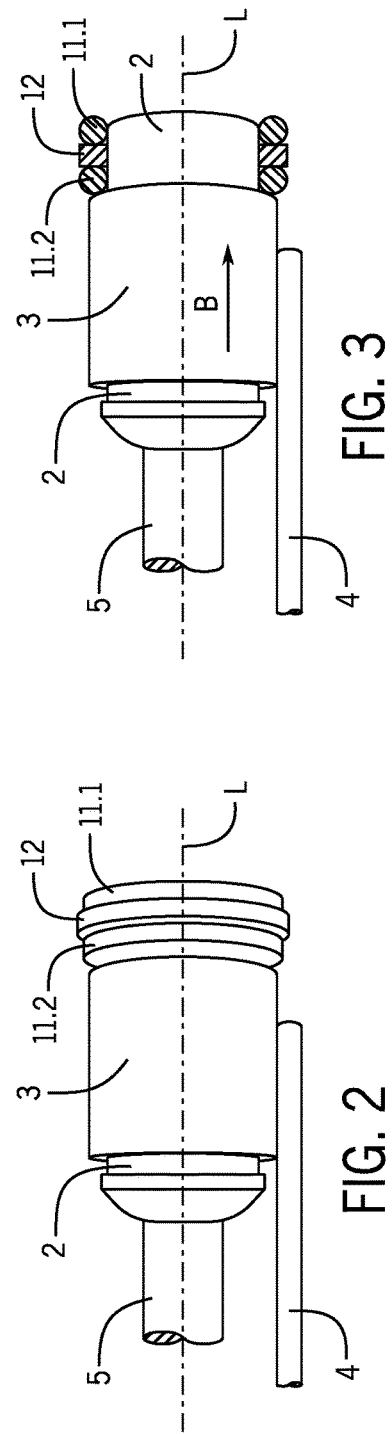

LIGATOR SYSTEM WITH AN INTERMEDIATE RING BETWEEN THE RING BANDS

FIELD OF THE INVENTION

The invention relates to a ligator system and an intermediate ring for such a ligator system.

BACKGROUND OF THE INVENTION

A band ligation is generally understood to be the application of an elastically expanded ring band to the anatomical region of a living organism to be ligated by the ring band in its relaxed state.

A ligator system is generally comprised of a medical device referred to as a ligator, with which the ring bands serving for ligation are pulled over the anatomical region to be ligated, and the associated ring bands.

For this purpose, the ligator typically has a holding tube on whose outer circumference the ring band is placed. In the process, the ring band is stretched, so that the inner diameter of the ring band is enlarged considerably. The holding tube is put over the anatomical region to be treated, and the tissue to be ligated is brought into the holding tube, for example by being sucked in by the latter. Then, the ring band is pushed towards the distal end of the holding tube to such an extent that it comes off the holding tube; graphically speaking, this is referred to as "firing" the ring band, even though the process is of a purely mechanical nature. Once the ring band has come off the holding tube, it abruptly contracts elastically and thus ligates the anatomical region thus treated.

US 2006/0259 A1 discloses an endoscopic device with intermediate members which are radially deformed by means of pulling means so that the deformed intermediate member is no longer an obstacle to the next band being stripped off.

US 2011/0106116 A1 discloses a device for sealing openings in tissues. In the process, the band for sealing tissue is discharged in a controlled manner and placed by means of an actuating lever. These bands have not intermediate members; furrows that are integrally connected to the holding tube are placed on the latter.

It is desirable to be able to place several ring bands one behind the other onto the holding tube, in order to be able to "fire" them successively in a controlled manner at different sites to be treated and thus be able to produce a ligature at different sites, without having to place another ring band onto the holding tube of the ligator again in between. In practice, however, there is the problem, on and off, that two ring bands are inadvertently peeled off the holding sleeve at the same time if an attempt is made to place the ring bands on the tube one behind the other, which results in one and the same region to be treated being ligated by two ring bands. This is not only uneconomical and counterproductive with regard to the desired rapid working progress, but also involves the risk of medical complications for various reasons.

It is therefore the object of the present invention to provide a ligator system which offers enhanced security against inadvertently firing off two ring bands at the same time.

SUMMARY OF THE INVENTION

The ligator system according to the invention is characterized in that two ring bands pushed one behind the other onto the holding tube of the ligator do not rest against each other directly, but are separated from each other by an intermediate ring pushed on between them. Viewed in the direction of the longitudinal axis of the holding tube, this intermediate ring keeps the two ring bands at a distance from each other. It is thus ensured that the next ring band, even after firing off the preceding ring band, still assumes a more than just insubstantial distance from the distal end of the holding tube, and therefore, even under unfavorable circumstances, does not come so close to the distal end of the holding tube that it inadvertently comes off the holding tube. This considerably simplifies the firing of the ring band, because it is no longer necessary to actuate the trigger in an extremely sensitive manner in order to thus ensure that, by advancing the ring bands along the longitudinal axis L of the holding portion for the purpose of firing the outermost ring band, only that ring band will actually disengage from the holding sleeve.

The invention enables the attending physician to restrict himself to retracting the ligator after firing for a short time in order to remove the intermediate ring. Then, the process can be continued by applying another ring band—without first having to laboriously pull a new ring band onto the holding sleeve of the ligator. In particular, this facilitates ligation for the treatment of hemorrhoidal complaints, but also of internal and external mucosal prolapses, of hemorrhages to be checked (e.g. in the intestinal tract, or also the ligation of other tissues to be removed in the region of the intestinal tract). Because pulling on a new ring band, which is yet to be expanded while being pulled on, onto the holding sleeve of a ligator that has already been used is considerably more difficult to manage, with regard to hygienic aspects, than merely taking off an intermediate ring that is no longer needed. In addition, the expenditure with regard to personnel and instruments can be reduced, and costs can also be saved with regard to the otherwise necessary sterilization measures (time and material as well as chemicals/disinfectants/packaging material).

Preferably the intermediate ring(s) is/are made from a material different from that of the ring bands. For the intermediate rings that do not come into contact with the body for a longer period of time, a less expensive material may be used, and the material of the intermediate rings can thus be adapted to the function of the intermediate rings, which have to be substantially less expansible than the ring bands.

It is expedient if the intermediate ring is made of a material whose spring stiffness D is greater by at least the factor 5 and ideally even by at least the factor 7.5 than the spring stiffness of the material of which the ring bands are made. It is thus ensured that the intermediate ring has a considerably smaller tendency to inadvertently come off the holding tube of the ligator than the ring bands have. Furthermore, it is thus ensured that the intermediate ring is able to push the rubber ring in front and is not compressed in an unwanted manner by the following rubber ring. Intermediate rings of metal would also be conceivable, which would possibly be hygienically processed after use so that they can be reused.

Ideally, the width of the intermediate ring 12 in the direction parallel to the longitudinal axis L of the holding tube is greater than the width or the diameter of the ring bands parallel to the longitudinal axis L. A ratio of at least 1.5:1 or, even better, of at least 2:1 in favor of the width of the intermediate ring 12 has proved effective. This also contributes to the intermediate ring not coming off or being pulled off inadvertently from the holding portion of the ligator. Due to its larger width, the intermediate ring has a secure purchase on the holding portion of the ligator.

Expediently, the intermediate ring rests against the surface of the holding tube only locally. Ideally, this is done by the intermediate ring having on its inner circumferential face at least three projections or tabs extending in a radially inward direction, with which it rests against the circumferential surface of the holding tube. In this way, even if a relatively hard material is used for the intermediate ring, it is easier to obtain a defined bias of the intermediate ring in relation to the surface of the holding tube than in the case of a contact of the surface of the entire inner circumference of the intermediate ring. The frictional resistance, and thus the force to be applied during application, can also be reduced thereby. Therefore, greater dimensional tolerances can be allowed for the intermediate ring, which not least accommodates the need for configuring the intermediate ring as a disposable component that is as inexpensive as possible and is discarded after a single application.

Preferably, the intermediate ring is adapted to the holding tube of the ligator in such a manner that, when it is pushed onto the holding tube, it undergoes an elastic deformation and thus rests against the surface of the holding tube, biased in such a way that it can only be displaced on the holding tube by overcoming a more than just inconsiderable friction. In this way, the friction between the outer surface of the holding tube and the intermediate ring can readily be adjusted in such a way that the intermediate ring is not lost inadvertently and prematurely.

Ideally, the smallest inner diameter of the intermediate ring is smaller by at least 0.1 mm and ideally by at least 0.2 mm than the outer diameter of the holding tube.

Protection is also sought for the intermediate ring as such, i.e. for an intermediate ring that serves for keeping at a distance from each other two or more ring bands pulled onto a holding tube of a ligator one behind the other, the inner diameter of the intermediate ring being adapted to the outer diameter of the holding tube of the ligator with which the intermediate ring is used as intended.

The advantage of the intermediate ring according to the invention is not least that, if the size is adapted correspondingly, it can be used to upgrade an already existing ligator system that so far corresponds to the prior art to the extent it is in accordance with the invention. Because on most ligators, there is a free holding portion available which, seen in the direction of its longitudinal axis, is wider than the diameter of a ring band, which makes it possible to pull at least two ring bands and an interposed intermediate ring onto the holding portion of the existing ligator.

Accordingly, protection is also sought for the use of the intermediate ring according to the invention for upgrading already existing ligators with different lengths and different diameters.

Furthermore, independent protection is also sought for a method for placing a ring band, which is carried out as follows:

For carrying out the method, a ligator is used onto whose holding portion, seen in the direction of the longitudinal axis of the holding portion, at least two ring bands are pulled one behind the other, which are separated from each other by an intermediate ring. In order to generate a ligation at a first site to be treated, only one ring band is fired off at first. Then, the ligator is retracted and the intermediate ring is removed. Then, the ligator is guided to a second site to be treated, at which another ligation is generated by means of the second ring band that is still located on the holding portion of the ligator. Separated by another intermediate ring, a third or fourth rubber ring may then be pulled on and fired off separately, if necessary.

Moreover, independent protection is sought for the use of at least one loose intermediate ring, i.e. an intermediate ring that can be completely removed from the holding portion (without tools), for applying expanded ligature rings, without reloading in the meantime, to an anatomical region of a living organism to be ligated by the respective ligature ring in its relaxed state using a ligator, which comprises a holding tube that accommodates in its interior the anatomical region respectively to be ligated and with its outer face keeps several ligature rings stretched wide, which are arranged (preferably aligned one behind the other), wherein the claimed use is characterized in that the intermediate ring is used for keeping at a distance from each other two ligature rings pulled, one behind the other preferably in alignment, onto a holding tube of a ligator, wherein the inner diameter of the intermediate ring is adapted in such a manner to the outer diameter of the holding tube of the ligator with which the intermediate ring is used as intended, that the intermediate ring is held on the holding tube preferably by frictional forces that are large enough to prevent, when a ligature ring is fired intentionally, another ligature ring from inadvertently coming off the holding ring. In the process, the intermediate ring is preferably used in such a way that it is discarded after a single application.

The expression "reloading in the meantime" is understood to mean the pulling on of another ligature ring onto the holding portion after firing off two ligature rings. The decisive point in this respect is that the complete removal of an intermediate ring from the holding portion can also be easily managed by the gloved hand of the operating surgeon and therefore causes no real interruption of the workflow. This is totally different when pulling on a ligature ring, which generally has to be expanded to a great extent using a corresponding device in order to be capable of being pulled onto the holding portion, which cannot be done "in passing" with a gloved hand, without interrupting the workflow.

Further mechanisms of action, advantages and optional embodiments of the invention become apparent from the following description of an exemplary embodiment with reference to the Figures.

BRIEF DESCRIPTION OF THE DRAWINGS

FIG. 1 shows a ligator as used in the ligator system according to the invention.

FIG. 2 shows an enlarged view of the holding section of the ligator shown by FIG. 1, which is equipped with two ring bands and an intermediate ring.

FIG. 3 shows the same ensemble as FIG. 2, with the difference that, here, the two ring bands and the intermediate ring are depicted in section.

FIG. 4 shows a detailed view of an exemplary embodiment of the intermediate ring according to the invention.

DETAILED DESCRIPTION OF THE PREFERRED EMBODIMENTS

Figure 5:
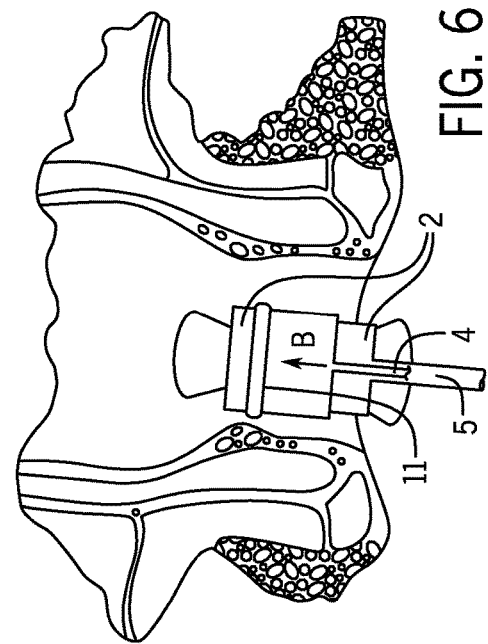
FIG. 5 schematically shows a single hemorrhoid in an anal channel, which also only shown schematically.

As is generally known, ring band ligation can be used for various medical indications and at different sites of the human or animal body. In principle, the ligator system according to the invention is suitable for all conceivable cases of applications, but is ideally used for the treatment of hemorrhoidal complaints. There, its strengths are particularly effective because it extremely facilitates the handling of the ligator in this hygienically critical area.

FIG. 1 shows a ligator 1 which is known as such and which is used for the ligator system according to the invention. This is a fully manually actuated ligator in which the firing is also manually triggered. Such a ligator has a particularly simple structure and is easy to sterilize, but, when firing, possibly behaves in a more critical manner than a ligator in which firing is carried out by means of an electric drive, which is able to work very precisely and advance the ring bands with a precision of fractions of a millimeter.

Typically, such a ligator consists of a grip 6, with which a holding tube 2 is connected via a connecting piece 5. An advancing tube 3, which is connected to a trigger 7 via an advancing rod 4, slides on the holding tube 2. For this purpose, the trigger 7 in the exemplary embodiment described here is pivotably mounted in the bearing block 9 supported by the connecting piece 5. The trigger 7 can be pulled in the direction of the arrow A and then transmits its movement via the connecting bearing 10 onto the advancing rod 4 in such a way that the advancing tube 3 is moved in the direction of the arrow B. In this way, the ring band 11, which is so far kept stretched wide by the holding tube 2, can be pushed along the holding tube 2 towards the distal end thereof and thus be "fired off"—once the ring band 11 has reached the distal end of the holding tube 2, it comes off the holding tube 2 under the influence of its elasticity or the energy stored in it due to being stretched, and contracts abruptly, whereby a ligation is generated at the respective site.

The holding portion 2 can be sealed at its proximal end and transition into the connecting piece 5, as is shown here in the Figures. Alternatively, the holding tube 2 may also be open at its proximal end, in order thus to enable the gripping of the site to be treated by means of a pair of forceps, using negative pressure (air suction system) or the like through the interior of the holding tube 2, such as is indicated, for example, by FIG. 6.

What is to be noted in the ligator shown in FIG. 1 is the clamping screw marked with the reference sign R. If this is disengaged, the position can be set that the advancing tube 3 assumes on the holding tube 2 when the trigger 7 has not been actuated. Whether the ligator system is loaded with one or several ring bands and intermediate rings according to the invention can be set in this manner. Thus, the space can be specifically provided on the holding tube 2 that is required for pulling the intermediate ring according to the invention onto the holding tube 2 in addition to the ring bands.

Figure 6:
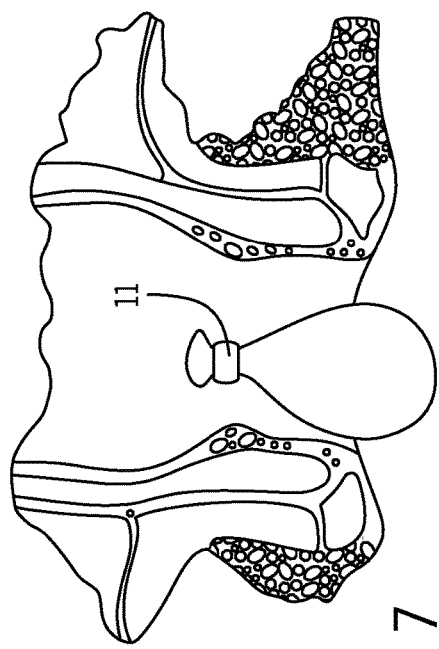
FIG. 6 shows the holding portion of the ligator put over the hemorrhoid shown by FIG. 5, just before firing off the ring band.
Figure 7:
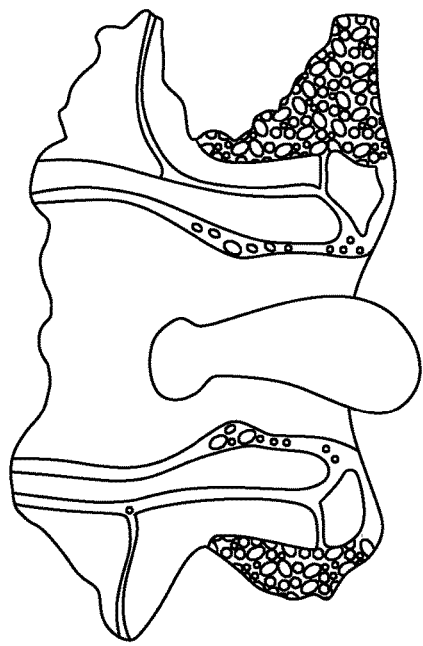
FIG. 7 shows the finished ligation generated with the means of FIG. 6.

FIGS. 5 to 7 show the generally known principle of ring band ligation for the special case of the treatment of hemorrhoids in order thus to illustrate the preferred environment of use of the ligator system according to the invention.

First, a look must be taken at FIG. 5. Here, the anal channel is shown schematically with a single hemorrhoid, which in this case is, of course, shown in a rough sketch.

In this case, ring band ligation is carried out in the manner shown in FIG. 6.

Using an anoscope, coloscope, rectoscope or proctoscope, which is known to the person skilled in the art and which is therefore not shown in the drawing, the above-described ligator is guided to the hemorrhoid or the tissue until finally the holding tube 2 of the ligator is placed to a large extent over the hemorrhoid so that the base of the hemorrhoid is located in the region of the distal opening of the holding tube 2, i.e. the opening facing away from the grip 6. Now, the ring band 11 is "fired off" in the manner already described above.

The ligation produced in this manner is shown by FIG. 7. The hemorrhoid is ligated by the ring band 11, which has contracted back to its original very small diameter. After some time, it is generally automatically rejected by the body, including the ring band.

While FIG. 1 shows a ligator system in which only a single ring band is pulled onto the ligator, FIGS. 2, 3 and 4 show the important points of the invention.

FIG. 2 shows a part of the ligator according to FIG. 1, i.e. the part of the ligator in the region of the holding tube 2.

The last portion of the connecting piece 5, which transitions into the holding tube 2, can easily be seen. The advancing tube 3, which has a longitudinal axis L and is welded or otherwise connected to the advancing rod 4, can also be seen easily.

A first ring band 11.1, the intermediate ring 12 and a second ring band 11.2 are pulled one behind the other onto the free portion of the holding tube 2, viewed in the direction of its longitudinal axis L.

FIG. 3 shows the same situation, with the first ring band 11.1, the second ring band 11.2 and the intermediate ring 12 being shown in section, however.

Referring to the FIGS. 2 and 3, it is easy to imagine that the first ring band 11.1 is fired once the advancing tube 3, by means of the advancing rod 4, is pushed a bit towards the right-hand side in the direction of the arrow B. In this case, the decisive fact is that the second ring band 11.2, which is still located on the holding tube 2, is still some way distant from the distal end of the holding tube 2 even after the first ring band 11.1 has been fired, and that there is therefore no risk that this second ring band 11.2 is also fired off inadvertently. This is due to the intermediate ring 12. This makes it unnecessary that the second ring band is also pushed close to the distal end of the holding tube 2 for firing off the first ring band, unlike those cases that have become known in the prior art and in which the two ring bands rest directly against one another.

FIG. 4 shows the intermediate ring 12 according to the invention. It is expedient if the intermediate ring has a cross section which substantially corresponds to the cross section of the holding tube and is preferably circular. Ideally, the intermediate ring 12 is seated on the holding tube 2 not with a certain play, but rather comes to rest against it with a certain bias when it is pulled onto the holding tube 2. For this purpose, the inner diameter of the intermediate ring 12 is typically smaller by 0.1 mm to 0.5 mm, if necessary up to 0.75 mm, than the outer diameter of the holding tube 2 onto which the intermediate ring 12 is pulled.

In order to obtain a defined friction between the intermediate ring 12 and the holding tube 2, it may be expedient to ensure that the intermediate ring 12 rests against the holding tube 2 only in a point-shaped manner or locally, and not along its entire inner circumference. To achieve this, the inner ring 12 can be provided with inwardly protruding tabs 13. Ideally, three tabs are used which, in pairs, respectively include an angle α of about 120°, see FIG. 4. Of course, the number of tabs 13 may also be higher, even though the use of only three tabs has proven very advantageous, because this enables the intermediate ring 12 to be easily pulled onto the holding tube 2.

Ideally, the width of the intermediate ring 12 in the direction parallel to the longitudinal axis L is greater than the width or the diameter of the ring bands parallel to the longitudinal axis L. A ratio of at least 1.5:1 or, even better, of at least 2:1 in favor of the width of the intermediate ring 12 has proved effective. This ratio is not shown in the Figures.

If a ligator is used whose holding tube is configured to be correspondingly long in the direction of its longitudinal axis L, three ring bands 11 separated by two intermediate rings 12 may of course also be pulled onto the holding tube. An even greater number is also theoretically conceivable, although not necessarily feasible.

The ring bands are usually made of a rubber-elastic material whose inner diameter is typically expanded by at least 100%, better by at least 200% or even more when the ring band is pulled onto the holding tube 2. In their undeformed state, the ring bands have a substantially rectangular cross section. In contrast, the intermediate ring 12 is made of a different material, which is preferably also a plastic, in order to be able to make the intermediate ring available as an inexpensive disposable part. However, the internal diameter of the intermediate ring 12 is usually expanded by less than 10%, most frequently even less than 5%, by pulling the intermediate ring onto the holding tube 2. Generally, the intermediate ring 12 is made of a material whose spring stiffness D is greater by at least the factor 5, most frequently even by at least the factor 10, than the spring stiffness of the material of which the ring bands 11 are made.

The invention claimed is:

1. A ligator system for the application of an expanded ligature ring to an anatomical region of a living organism to be ligated by the ring in its relaxed state, the ligator system comprising:
a ligator having a holding tube and an advancing tube, wherein the holding tube is able to accommodate in its interior the anatomical region to be ligated and to keep with its outer face several ligature rings, which are disposed one behind the other, stretched wide, wherein the ligator system further comprises at least two ligature rings and at least one intermediate ring, which is made from a different material than the ligature rings and is disposed on the holding tube between two ligature rings and keeps the two ligature rings at a distance from each other in a direction of a longitudinal axis of the holding tube, and wherein the two ligature rings and the intermediate ring located between them are disposed on the holding tube of the ligator in such a way that, by way of the advancing tube, the two ligature rings and the intermediate ring can be pushed together along the holding tube in a direction towards a distal end thereof in order to fire one of the ligature rings.

2. The ligator system according to claim 1, wherein the intermediate ring is made of a different plastic material than the ligature rings.

3. The ligator system according to claim 1, wherein the intermediate ring has a spring stiffness that is greater by at least a factor of 10 than a spring stiffness of the at least two rings.

4. The ligator system according to claim 1, wherein the intermediate ring, in relation to its intended mounting position on the holding tube, has a width in the direction of the longitudinal axis of the holding tube that has more than 1.5 times an extent of the at least two ligature rings when the at least two ligature rings is located at its intended mounting position on the holding tube.

5. The ligator system according to claim 1, wherein the intermediate ring with at least three projections extending in a radially inward direction rests against the holding tube only at the three projections.

6. The ligator system according to claim 1, wherein the intermediate ring is adapted to the holding tube in such a manner that, when the intermediate ring is pushed onto the holding tube, the intermediate ring undergoes an elastic deformation and thus rests against a surface of the holding tube, biased in such a way that the intermediate ring can only be displaced on the holding tube by overcoming friction that is large enough to prevent, when a ligature ring is fired intentionally, another ligature ring from inadvertently coming off the holding ring.

7. The ligator system according to claim 1, wherein a smallest inner diameter of the intermediate ring is smaller by at least 0.1 mm to 0.5 mm than the outer diameter of the holding tube.

8. The ligator system according to claim 1, wherein the ligator system comprises a plurality of intermediate rings which are each configured as a disposable article that is discarded after each use.

9. The ligator system according to claim 1, wherein the intermediate ring is made from metal.

10. The ligator system according to claim 1, wherein the intermediate ring is made from plastic.

11. The ligator system according to claim 1, wherein the intermediate ring rests against a surface of the holding tube only at 3 to 4 points spaced apart from each other in a defined manner.

* * * * *